United States Patent [19]

Grier-Idris

[11] Patent Number: 4,957,120
[45] Date of Patent: Sep. 18, 1990

[54] SURGICAL DRAPE WITH EXTREMITY POUCH

[75] Inventor: Carletta Grier-Idris, Acworth, Ga.

[73] Assignee: Kimberly-Clark Corporation, Neenah, Wis.

[21] Appl. No.: 474,694

[22] Filed: Feb. 6, 1990

Related U.S. Application Data

[63] Continuation of Ser. No. 246,041, Sep. 16, 1988, abandoned.

[51] Int. Cl.$^5$ ............................................. A61F 13/00
[52] U.S. Cl. .................................. 128/849; 128/853
[58] Field of Search .................................. 128/849–856

[56] References Cited

U.S. PATENT DOCUMENTS

| | | | |
|---|---|---|---|
| 1,554,692 | 9/1925 | Shane | 128/849 |
| 2,715,902 | 8/1955 | Shaffer | 128/853 |
| 3,182,656 | 5/1965 | Pyne | 128/853 |
| 3,503,391 | 3/1970 | Melges | 128/132 |
| 3,769,971 | 11/1973 | Collins | 128/132 D |
| 3,889,667 | 6/1975 | Collins | 128/132 D |
| 3,910,628 | 10/1975 | Miller | 128/132 D |
| 3,926,185 | 12/1975 | Krzewinski | 128/132 D |
| 3,930,497 | 1/1976 | Krebs | 128/853 |
| 3,934,582 | 1/1976 | Gorrie | 128/157 |
| 3,968,792 | 7/1976 | Small | 128/132 D |
| 3,989,040 | 11/1976 | Lofgren | 128/856 |
| 4,051,845 | 10/1977 | Collins | 128/855 |
| 4,119,093 | 10/1978 | Goodman | 128/132 D |
| 4,253,451 | 3/1981 | Solomon | 128/132 D |
| 4,308,864 | 1/1982 | Small | 128/856 |
| 4,457,026 | 7/1984 | Morris | 128/851 |
| 4,462,396 | 7/1984 | Wichman | 128/853 |
| 4,471,769 | 9/1984 | Lockhart | 128/132 D |
| 4,479,492 | 10/1984 | Singer | 128/132 D |
| 4,570,628 | 2/1986 | Neal | 128/132 D |
| 4,586,498 | 5/1986 | Morris | 128/132 D |
| 4,679,552 | 7/1987 | Caspari | 128/132 D |
| 4,730,609 | 3/1988 | McConnell | 128/853 |

*Primary Examiner*—Robert A. Hafer
*Assistant Examiner*—Michael Brown
*Attorney, Agent, or Firm*—Patrick C. Wilson

[57] ABSTRACT

Disclosed herein is a surgical drape with an external extremity pouch for use in conjunction with limb surgery. Drapes used in such surgery are typically of sufficient size to completely cover the patient and extend down over the sides of the operating table. Such drapes are further provided with a fenestration to permit the extension of the limb through the drape from the underside to the external surface of the drape. The drape of the present invention has an extremity pouch attached to the external surface of the drape on the portion which hangs over the side of the operating table. The pouch is adapted to receive and isolate an exposed limb such as a leg or arm should it become necessary to extend the limb over the side of an operating table during a surgical procedure.

4 Claims, 3 Drawing Sheets

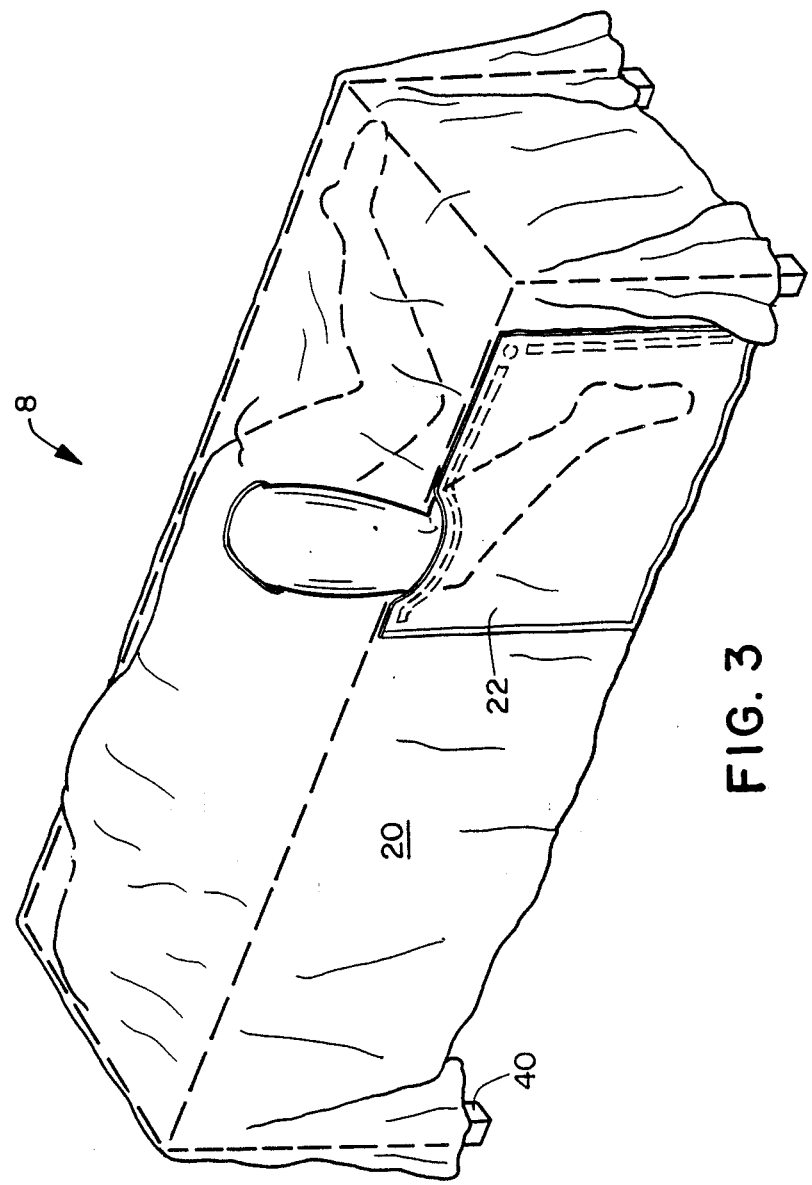

SURGICAL DRAPE WITH EXTREMITY POUCH

This is a continuation of co-pending application Ser. No. 07/246,041 filed on Sept. 16, 1988, now abandoned.

BACKGROUND OF THE INVENTION

This invention relates to a surgical drape for use in conjunction with limb surgery. More particularly it relates to a surgical drape with an extremity pouch for receiving a limb should it become necessary to extend the limb off and below the top of the operating table during a surgical procedure.

Surgical drapes are used to isolate the operative site from the remainder of the patient in an effort to keep the site sterile and reduce the chances of infection or contamination. In hip, leg, knee, shoulder and arm surgery one type of surgical drape includes a large main sheet which is designed to completely cover the patient and hang down over the sides of the operating table. To expose the limb or joint for surgery, the main sheet is provided with a fenestration through which the limb is extended from the underside of the drape. Two examples of such drapes are the Orthopedic Pack I and Orthopedic Pack V drape assemblies manufactured and sold by the Kimberly-Clark Corporation. To further isolate the limb, additional draping may be used around the limb itself. See for example U.S. Pat. Nos. 3,769,971 to Collins, 3,934,582 to Gorrie, 3,968,792 to Small, 3,989,040, 4,253,451 to Solomon, 4,308,864 to Small, et al. and 4,679,552 to Caspari. Limb drapes such as are shown in the previously cited 3,934,582; 3,968,792 and 3,989,040 references are sometimes referred to as stockinettes due to their crude resemblance to a stocking and a similar method of donning. Alternatively, the stockinette may be directly attached to the main sheet about the fenestration as is shown in U.S. Pat. No. 4,119,093 to Goodman.

Limb surgery, and in particular hip surgery, often requires that the limb be moved into a number of positions. As part of good sterile operating room procedure or technique, the limb should normally remain at or above the plane defined by the top of the operating table as all parts of the operating room, personnel and equipment below and outside this plane are considered to be non-sterile. This is despite the fact that all fixed equipment is kept as clean as possible and all surgical tools, gowns and drapes are sterilized prior to their use. Ever mindful of the requirements of good sterile technique, operating room personnel find it sometimes necessary to extend the limb over and off the operating table. In so doing, the limb may extend below or off the top of the table and therefore below the plane of what is considered the sterile operating room field. During this time the limb may come in contact with the gowns of operating room personnel as they work near or against the operating table. This in turn increases the risk that the limb may be contaminated by such contact. As a result there is a need for a drape design which will maintain the limb in as sterile a condition as is possible while it is off the operating room table.

With the rise in concern over the transmission of infectious diseases through such body fluids as blood, there is also an increased concern in protection of operating room personnel from such fluids. To help protect against such situations, gowns worn by operating room personnel are often supplemented in the chest area by a fluid impervious material such as a plastic film laminated to the gown material. While these laminated areas provide greater resistance to liquid strike-through, they also make the gown hotter and more uncomfortable to wear. As a result, the use of such plastic film is limited to the chest area and does not always extend below waist level. Consequently, should operating room personnel contact a limb which is hanging below the operating table, the surgical gown may provide only limited resistance to fluid strike-through. Therefore, there is a need for a surgical drape with increased protection and isolation of limbs during surgery.

It is therefore an object of the present invention to provide a surgical drape for limb surgery which has one or more extremity pouches located laterally on a portion of the drape which hangs below the table.

It is a further object of the present invention to provide an extremity pouch which has one or more detachable sides to permit easy insertion of the limb into the pouch and subsequent extraction therefrom.

These and other objects and advantages of the present invention will become more apparent from a further review of the following specification, drawings and claims.

SUMMARY OF THE INVENTION

The present invention relates to a surgical drape with an extremity pouch for use in conjunction with limb surgery. In certain instances during limb surgery, as for example hip surgery, it has been found that the procedure is facilitated by extending the limb/leg over the side of the table during a portion of the operation. Unfortunately, in so manipulating the leg, it is taken from what is referred to as a sterile portion of the operating field into a non-sterile portion. This is because all areas below the plane of the operating table top are considered non-sterile despite the fact that the operating room is kept as clean as possible and all surgical instruments, drapes, covers and gowns have been sterilized prior to their use. To assist in keeping the limb isolated when it is extended off and below the operating table, the drape of the present invention is provided with an extremity pouch on the exterior of the drape. The pouch has one or more adjacent sides which are openable to permit insertion and extraction of the limb from the pouch. Alternatively, one or more adjacent sides of the pouch may be releasably fastened to the exterior side of the drape so that the pouch can be opened for insertion of the limb and then refastened to further isolate the limb and keep foreign objects such as sponges, etc., from falling into the pouch and to prevent the pouch from billowing.

BRIEF DESCRIPTION OF THE DRAWINGS

FIG. 3 is a perspective view of a surgical drape with extremity pouch according to the present invention in use on an operating table with a leg inserted into the pouch.

DESCRIPTION OF THE PREFERRED EMBODIMENTS

Figure 1:
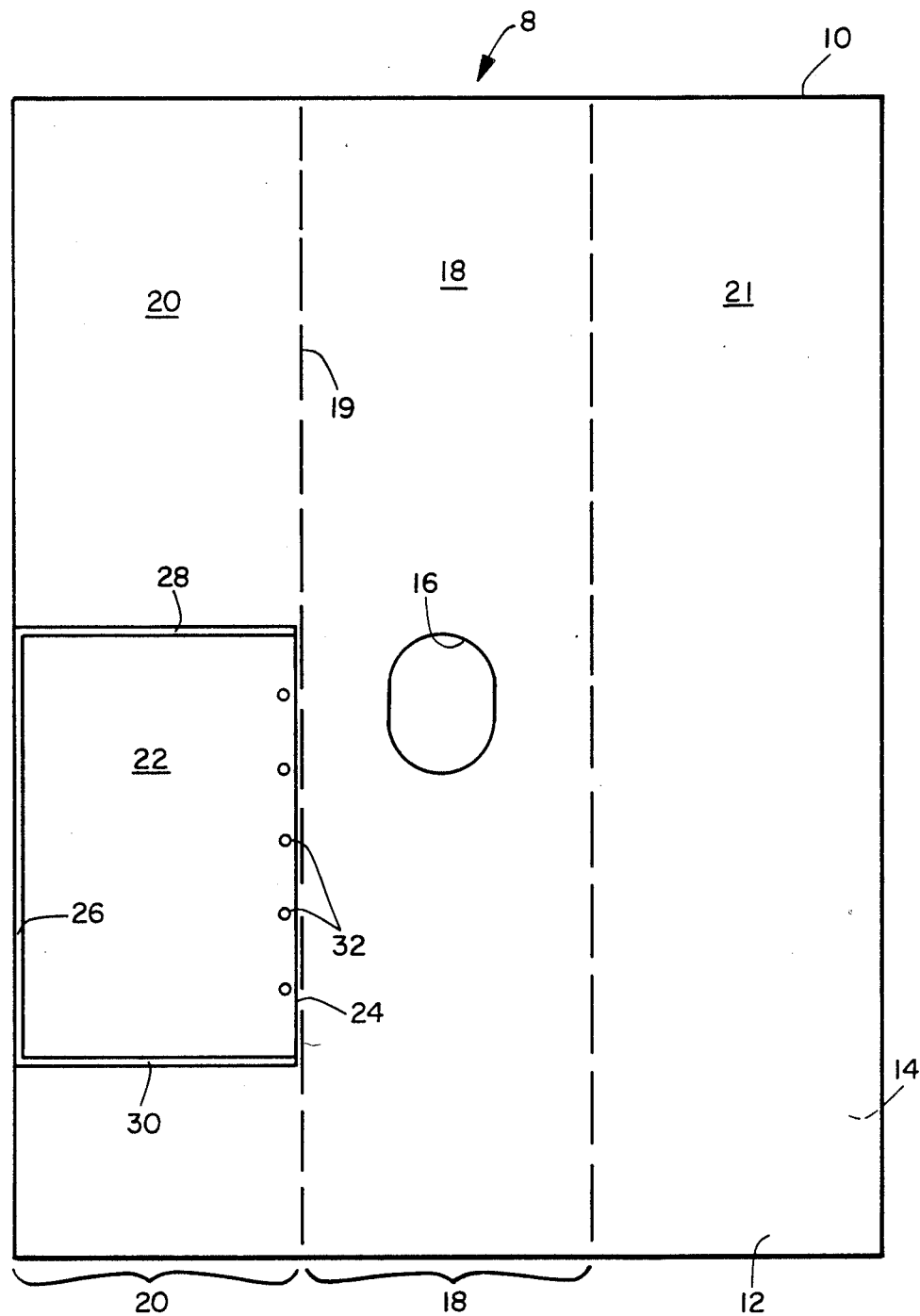
FIG. 1 is a plan view of a surgical drape with an extremity pouch according to the present invention.

Turning to FIG. 1 there is shown in plan view a surgical drape with extremity pouch according to the present invention. For purposes of illustration only, the drape shown in the figures is used in conjunction with leg surgery. It should be understood, however, that the drape of the present invention is compatible with limb and joint surgery in general and therefore encompasses surgical procedures involving the arm, hip, knee and shoulder.

The drape 8 includes a main sheet 10 having a top or external surface 12 and a bottom surface 14 with a fenestration 16 of sufficient size to permit a limb to be extended therethrough from the bottom surface 14 to the external surface 12 so as to expose the limb for surgery while isolating the remainder of the body. Alternatively, the drape may include a split in addition to or in lieu of the fenestration 16. Such drapes are commonly referred to as split sheets or, for example, bilaterial split sheets as shown in commonly assigned U.S. Pat. No. 4,479,492 to Singer which is incorporated herein by reference. In addition the fenestration in the drape may be replaced by a "U" drape. Thus, the fenestration may be defined as a hole, a split or a "U" cut-out in the drape or a combination of the foregoing.

Generally, the main sheet 10 should be of sufficient size to completely cover a body on an operating table and in addition hang down several feet over the sides of the operating table. A typical size would be 80 inches wide by 130 inches long. A drape of this general size is foldable into at least a first section 18 and a second section 20 separated by a fold line 19. See FIG. 1. The first section 18 includes the fenestration 16 and the portion of the drape 10 which covers the patient and the top of the operating table 40 shown in phantom in FIG. 3. The second portion 20 is the part of the drape 8 which hangs down over the side of the operating table 40. In all likelihood, the drape 8 will have a third portion 21 which is similar to and opposite from second portion 20.

Figure 2:
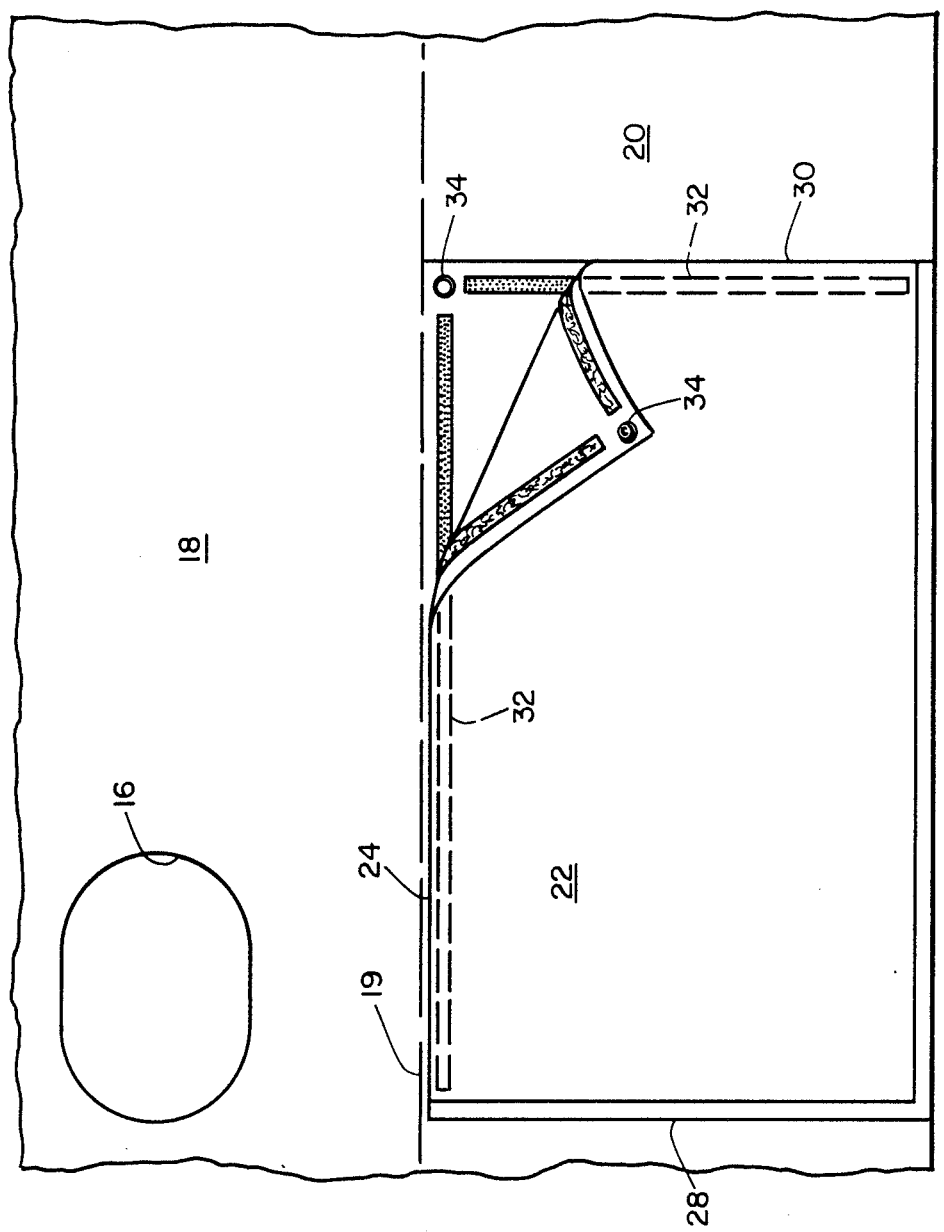
FIG. 2 is an isolated view of the extremity pouch, from FIG. 1 in a partially opened state according to the present invention.

Positioned on the external surface 12 of the second portion 20 of main sheet 10 is an extremity pouch 22. The pouch 22 can take a number of various shapes. As shown in FIGS. 1 through 3 the pouch 22 is rectangular in shape with a top edge 24 and a bottom edge 26 joined by a first side edge 28 and a second side edge 30. Securement of the pouch 22 via its periphery to the main sheet 10 can be by any means known to those skilled in the art, such as stitching or adhesives, the only proviso being that the means of attachment is capable of withstanding subsequent sterilization techniques as by steam or ethylene oxide. Suitable materials for the pouch include cloth, nonwovens, plastic films and combinations thereof with films providing added resistance to fluid strike-through.

The pouch 22 is positioned on the second portion 20 of the main sheet 10 most preferably adjacent the fold line 19 near the fenestration 16. Depending upon the type (leg or arm) and size of the limb, the optimum placement of the extremity pouch 22 may vary. As a result, it may be advantageous to make the pouch 22 slightly oversized to accommodate a variety of situations. In general, however, the pouch 22 should be of sufficient size and proximity to the fenestration 16 to permit the lower portion of the limb (from the knee down with respect to the leg and from the elbow down with respect to the arm) to be positioned within the pouch.

In the embodiment shown in FIG. 1, the top edge 24 is open to allow insertion/extraction of the limb and the remaining edges 26, 28 and 30 are closed and secured to the main sheet 10. If desired, the top edge 24 of pouch 22, may also include a row of snaps 32 or other releasable fastening means which can be used to close the pouch 22 around the limb once it is inserted. This serves to further isolate the limb when it is in this position and it also helps to prevent objects such as sponges, etc., from falling into the pouch during surgery.

Alternatively, the pouch 22 may be open on two or more adjacent sides, as for example 24 and 30, and closed on the other two sides 26 and 28. The two open sides, 24 and 30, may be detachably secured to the main sheet 10 at their common corner by a fastener 34 such as a snap or Velcro TM as shown in FIG. 2. The advantage of this embodiment is that it allows the pouch 22 to be opened to a greater extent during insertion and extraction of the limb, thereby reducing the amount of bending of the limb which may be undesirable in the case of a severely damaged limb. As with the embodiment shown in FIG. 1, the pouch 22 in FIG. 2 also may be provided with additional snaps or other releasable fastening means 32 along its periphery to allow further isolation of the limb.

To use the surgical drape with extremity pouch of the present invention, the drape is placed over the patient and the limb is extended through the fenestration as normally would be the procedure. Any additional preparation of the patient/operating site is also carried out according to normal procedures for the particular type of surgery involved. Should it then become necessary during the course of the operation to lower the limb over the side of the operating table, the extremity pouch 22 is opened and the limb is inserted into the pouch. If the pouch 22 is further provided with snaps 32 or other types of closure means along the open sides, the snaps can be secured to further isolate the limb when it is below the sterile plane of the operating field. Should the limb later need repositioning, the limb is simply and quickly removed from the pouch and moved to the new position. Furthermore, should there be a subsequent need to extend the limb below the operating table, the extremity pouch 22 can again be brought into use.

Note that while the embodiments described and shown herein only have one pouch located on the exterior of the drape, multiple pouches also may be employed. For example, a second pouch can be placed on the third portion 21 of the main sheet 10 so that a limb can be positioned to either side of the operating table. Having thus described the invention in detail, it should be apparent to those skilled in the art that various modifications and changes can be made in the present invention without departing from the spirit and scope of the following claims.

We claim:

1. A surgical drape for use in limb surgery on an operating table having atop comprising a main sheet having an external surface and a bottom surface and a fenestration to permit a limb to be extended therethrough from said bottom surface to said external surface, said main sheet having a first section which is adapted to be positioned on said operating table top and includes said fenestration, and a second section which is adapted to hang below said operating table, and a pouch for receiving said limb when positioned below said operating table top, said pouch being secured to said external surface of said main sheet on said second portion, said pouch having a top edge and a bottom edge jointed by opposed first and second side edges, said first and second side edges and said bottom edge being secured to said main sheet and said top edge being detachably secured to said main sheet to allow said pouch to be opened to receive said limb and then closed after insertion of said limb.

2. The surgical drape of claim 1 wherein said second side edge is detachably secured to said main sheet.

3. The surgical drape of claim 2 wherein said second side edge and said top edge further include closure means for releasably closing said second side edge and said top edge to said main sheet.

4. The surgical drape of claim 2 wherein said top edge further includes closure means for releasable closing said top edge to said main sheet.

* * * * *

UNITED STATES PATENT AND TRADEMARK OFFICE
CERTIFICATE OF CORRECTION

PATENT NO. : 4,957,120

DATED : September 18, 1990

INVENTOR(S) : Carletta Grier-Idris

It is certified that error appears in the above-identified patent and that said Letters Patent is hereby corrected as shown below:

Column 4, line 65, "jointed" should read --joined--.

Signed and Sealed this

Second Day of March, 1993

Attest:

STEPHEN G. KUNIN

Attesting Officer

Acting Commissioner of Patents and Trademarks